United States Patent
Årthun et al.

[11] Patent Number: 6,032,543
[45] Date of Patent: Mar. 7, 2000

[54] DEVICE FOR INTRODUCTION AND/OR WITHDRAWAL OF A MEDIUM INTO/FROM A CONTAINER

[75] Inventors: Nils Årthun, Öckerö ; Sten Johansson, Hisings Kärra; Håkan Samuelsson, Onsala, all of Sweden

[73] Assignee: Novaseptum AB, Nödinge, Sweden

[21] Appl. No.: 09/068,320

[22] PCT Filed: Oct. 18, 1996

[86] PCT No.: PCT/SE96/01325

§ 371 Date: May 4, 1998

§ 102(e) Date: May 4, 1998

[87] PCT Pub. No.: WO97/16715

PCT Pub. Date: May 9, 1997

[30] Foreign Application Priority Data

Nov. 2, 1995 [SE] Sweden .................................. 9503870

[51] Int. Cl.[7] .................................................. G01N 1/12
[52] U.S. Cl. ........................................................ 73/863.84
[58] Field of Search ............................. 73/863.81, 863.82, 73/863.85, 863.86, 864.74, 863.83, 863.84, 864.51, 864.62, 864.11; 141/329, 330

[56] References Cited

U.S. PATENT DOCUMENTS

| | | | |
|---|---|---|---|
| 3,736,099 | 5/1973 | Begg et al. | 73/864.11 |
| 4,941,517 | 7/1990 | Galloway | 73/863.85 |
| 5,535,635 | 7/1996 | Shaw | 73/863.84 |

FOREIGN PATENT DOCUMENTS

| | | | |
|---|---|---|---|
| 2161702 | 6/1973 | Germany | 73/863.85 |
| 3701250 | 7/1988 | Germany | 73/864.11 |

*Primary Examiner*—Robert Raevis
*Attorney, Agent, or Firm*—Dvorak & Orum

[57] ABSTRACT

The invention concerns a device for introduction and/or withdrawal of a medium into/form an apertured container, and it comprises at least one transfer (1) for transferring medium to or from the container, and at leant one seal. The seal is incorporated as a sealingly mounted part of the transfer member (1) and the transfer member (1) is by means of a fastening device (3), via the seal, sealingly secured to the container of a fastening device (3), via the seal, sealingly secured to the container aperture during use and them forms a closed system together with the container. The transfer member (1) is removable for replacement thereof after use and the seal has a sealable channel to interconnect the transfer member (1) and the container interior during use.

14 Claims, 6 Drawing Sheets

DEVICE FOR INTRODUCTION AND/OR WITHDRAWAL OF A MEDIUM INTO/FROM A CONTAINER

The present invention relates generally to a device for introduction and/or withdrawal of a medium into/from a container, and more particularly to such devices for introduction and/or withdrawal of media into/from a container as are intended for use in areas with very strict requirements on low contamination risks inside the container and/or in the container environment.

Within for instance the pharmaceutical and biotechnology fields and to some extent in the food manufacturing and cosmetic industries there is a continuous need for sampling of media, for example for micro-biology checks, cell counts, or for chemical analysis, or for addition of regulating or active media, such a pH-buffer of a biological starting culture, during a certain processing step in the production of products within each field. When such production is carried out under conditions of low contamination requirements with respect to the media that are taking part in the process, the production normally is carried out in a sealed container. However, contamination risks arise when a medium is to be added to or a sample be withdrawn from the container.

One example of a prior-art device for withdrawing samples from a container for the above mentioned usages is shown in U.S. Pat. No. 3,779,082. The device comprises a self-sealing membrane disposed in an aperture in the container. A plurality of channels interconnect the membrane with the area exteriorly of the container. A transfer member fitted with a hypodermic needle may be received in one of the channels, it being possible to introduce the hypodermic needle through the membrane into communication with the container interior. In this manner samples may be withdrawn from the container or a medium be introduced into the container via the hypodermic needle. A vinyl tape or the like covers the upper ends of the channels until the transfer member is inserted into the channels. The device may be pre-sterilised, in which case the channels are not exposed to contamination risks until a transfer member is inserted therein.

A drawback inherent in this construction is that the upper part of the membrane may be contaminated in connection with the transfer member contacting the membrane. Impurities and the like may be drawn into the container via the hypodermic needle. In addition, a small amount of the medium will always accompany the hypodermic needle as the latter is withdrawn from the membrane. In this manner the area exteriorly of the container is exposed to contamination risks when this prior device is in use, which is particularly serious when for instance specimen of toxic media are being withdrawn.

In U.S. Pat. No. 3,776,042 is shown another device for withdrawal of samples from a container. This device comprises two self-sealing membrane parts which are sealingly disposed in a hose fitting in a container. An aseptic medium, such as steam or the like, flows from an inlet to an outlet in the hose fitting intermediate the membrane part. The hypodermic needle of a transfer member pierces the outer membrane part and is disinfected by the steam before being introduced into the inner membrane into communication with the container interior. In this position a sample may be withdrawn. When the hypodermic needle is pulled out, it is again sterilised by steam in the area intermediate the membrane parts.

The drawback inherent in this device is that to use steam requires expensive special equipment. Steam may be useful for sterilising against bacteria but this equipment cannot be used for sampling media that must not contaminate the environment and that are not destroyed by steam, since they may accompany the hypodermic needle as the latter is withdrawn from the two membrane parts or contaminate the area between the membrane parts or the steam tube system connected to the area between the membrane parts. In addition, the sample and the environment may come into contact with one another via the hypodermic needle tunnel, once the hypodermic needle has been withdrawn from the membrane parts, which in itself constitutes a contamination risk.

On account of the risks of contamination of the medium inside the container and the container environment, sampling or introducing of media normally are carried out in "clean rooms" by means of devices in accordance with prior-art technology, which envolves high investment costs for ventilation equipment, locks and the like, in addition to which the requirements on the personnel working in the "clean room" are particularly severe.

A first object of the subject invention thus is to provide a device for introduction and/or withdrawal of a medium into/from a container, according to which the medium upon and following withdrawal is protected from contamination from the environment.

A second object of the present invention is to provide a device for introduction and/or withdrawal of a medium into/from a container, according to which the environment is protected from contamination from the medium being withdrawn.

A third object of the present invention is to provide a device for introduction and/or withdrawal of a medium into/from a container, according to which the medium, when being introduced into the container, is protected from contamination from the environment.

A fourth object of the present invention is to provide a device for introduction and/or withdrawal of a medium into/from a container, according to which the environment is protected from contamination during introduction of a medium into the container.

A fifth object of the present invention is to provide a device for introduction and/or withdrawal of a medium into/from a container, according to which a sample that has been withdrawn from the container, is representative of the medium inside the container.

A sixth object of the present invention is to provide a device for introduction and/or withdrawal of a medium into/from a container, according to which the device may be used also outside "clean rooms".

These and other objects are achieved in accordance with the invention by means of a device for introduction and/or withdrawal of a medium into/from a container as defined in claim 1.

Other particularities and advantageous embodiments are defined in the dependent claims.

In the following will be described currently preferred embodiments of the present invention in closer detail with reference to the accompaning drawings, wherein.

Figure 1:
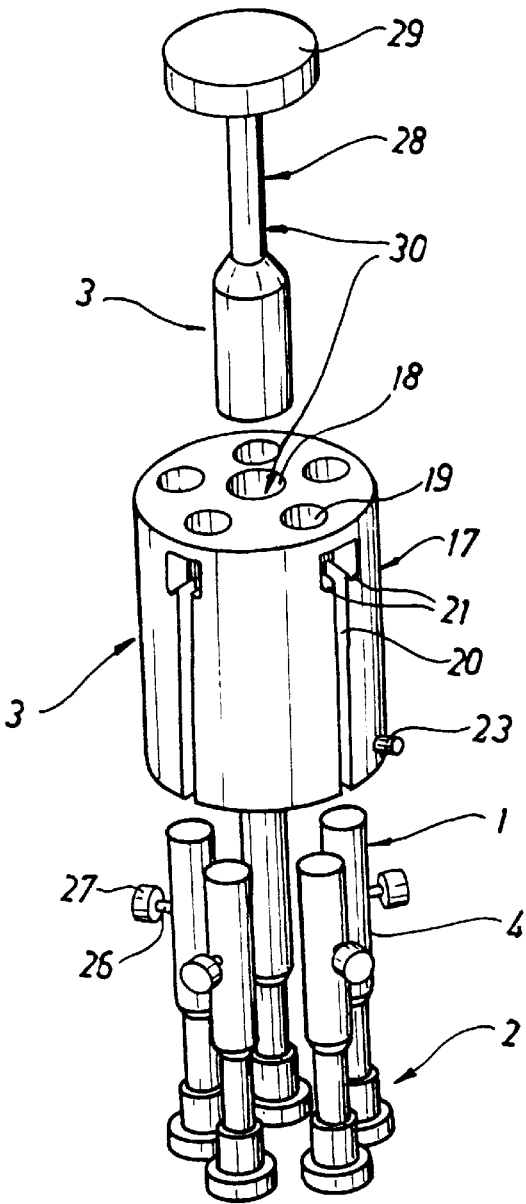
FIG. 1 is a schematical exploded view showing one embodiment of a device for introduction and/or withdrawal of a medium into/from a container.
Figure 1:
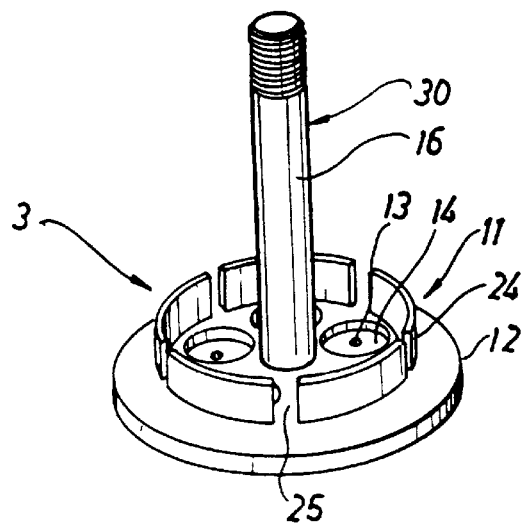

The device illustrated in FIG. 1 comprises five transfer members each one of which is designated generally by reference 1. In accordance with a preferred embodiment the transfer member 1 is an injector/ejector means. At its lower end each transfer member is formed with a seal, generally designated by reference 2. In addition, the device comprises a fastening device, generally designated by 3, which device consists of three parts.

Each transfer member 1 is provided with a holder 4. The holder encloses the upper end of a hypodermic needle 5. The lower edge of the holder 4 is formed with a downwardly open groove 6 having an essentially circular cross-sectional configuration.

The seal 2 is formed with an upper bellows-shaped part 7. At its upper end the bellows-shaped part 7 is formed with a bead 8 which is inserted in the groove 6, thus sealingly interconnecting the seal 2 and the holder 4. The bellows-shaped part 7 encloses the hypodermic needle 5 in the longitudinal direction thereof and it may be compressed in the lengthwise direction of the needle 5 between the positions illustrated in FIGS. 3 and 4, respectively. At its lower end the seal 2 is formed with a membrane portion 9 the upper end of which is sealingly attached to the bellows-shaped part 7. The membrane portion 9 is self-sealing and is pierceable by the tip 10 of the hypodermic needle.

The fastening device 3 comprises one flanged part, generally designated by reference 11. The flanged part 11 is formed with an essentially circular base plate 12 in which five through holes 13 are made, each having a diameter-size allowing passage therethrough of a hypodermic needle 5. About each hole 13, in the upper face of the base plate 12, is formed a seat 14, said seat being essentially centered about the hole 13. The lower end of the membrane portion 9 is formed with a collar 15 fitting the seat 14. From the upper face of the flanged part 11, projecting essentially perpendicularly therefrom, is arranged a stub axle 16 having a threaded upper end.

The fastening device 3 likewise comprises an essentially cylindrical magazine part, generally designated by 17. A centrally located, longitudinal through channel 18 passes through the magazine part 17, through which channel the stub axle 16 may project. In addition, the magazine part 17 is formed with five through apertures 19 extending in parallel with channel 18 and having a diameter-size corresponding to or slightly exceeding the diameter-sizes of the holder 4, the bellows-shaped part 7, and the upper end of the membrane portion 9 but being smaller than the diameter of the collar 15. The lower end of each aperture 19 is connected to a longitudinal outwardly open groove 20 provided in the peripheral surface of the magazine part 17 exteriorly of the associated aperture 19. At its upper end, the groove 20 is formed with two lateral recesses 21.

Figure 2:
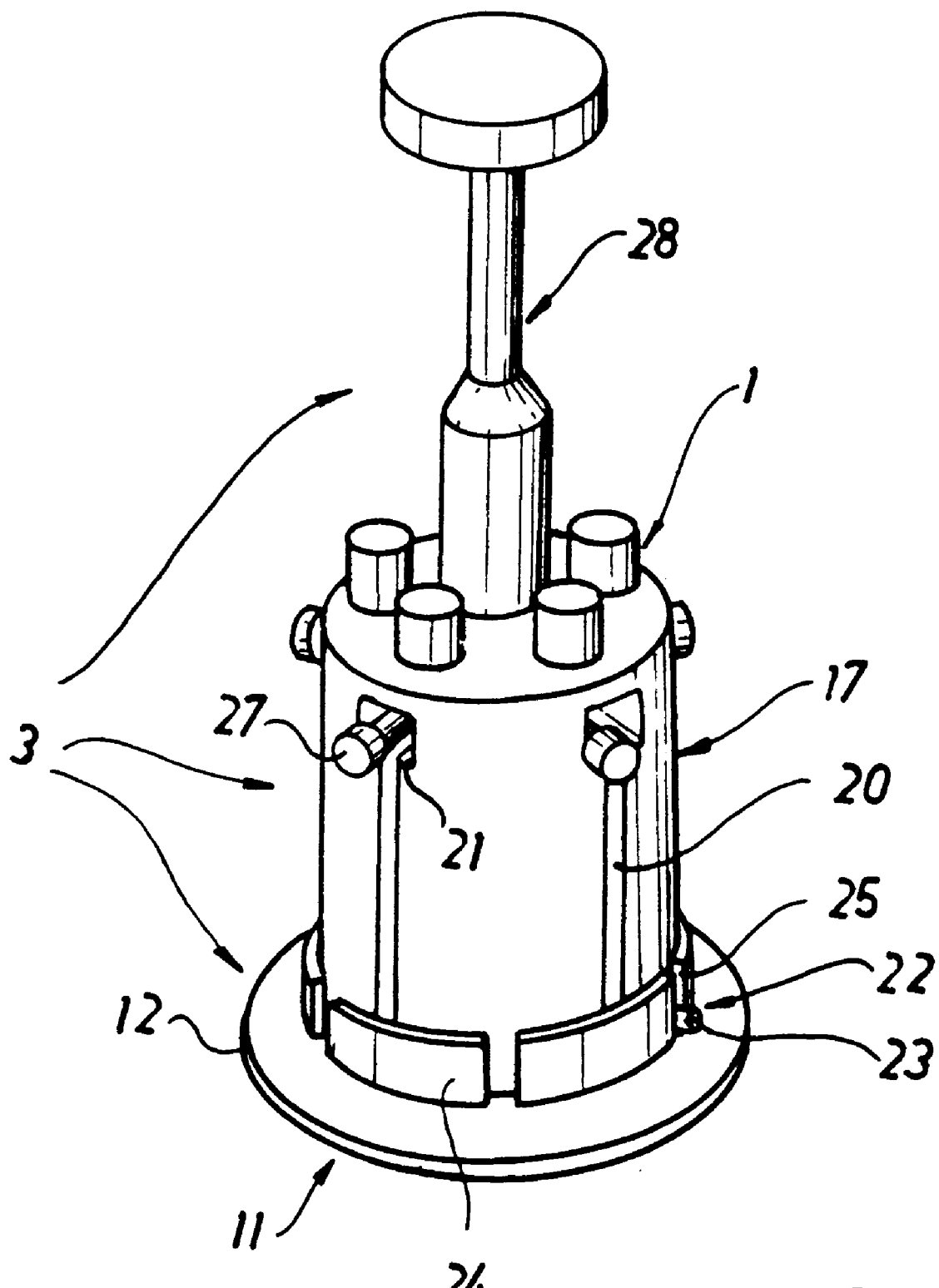
FIG. 2 illustrates the device of FIG. 1 schematically in its assembled condition.

The magazine part 17 and the flanged part 11 have a centering means generally designated by 22 (see FIG. 2). The centering means 22 comprises at least one pin 23 projecting essentially perpendicularly from the lower part of the peripheral surface of the magazine part 17. The flanged part 11 is formed on its upper face with an annular means 24 matching the cross-sectional area of the magazine part 17 so as to fit the exterior of the latter. The annular means 24 is formed with at least one slit 25 into which the pin 23 may be inserted.

The upper end of the hypodermic needle 5 is sealingly connected to a hose socket or fitting 26 which is receivable in the groove 20. The hose socket 26 may be formed with a peripheral stop shoulder 27 (see FIG. 1) alternatively, the hose socket 26 may in itself function as a stop shoulder (see FIGS. 3 and 4). In FIGS. 1 and 2 the stop shoulder 27 has a larger diameter-size than the groove 20 and is spaced such a distance from the holder 4 that the transfer member 1 may be introduced into the aperture 19 and the groove 20 from the lower end of the magazine part 17.

In addition, fastening device 3 comprises a locking part, generally designated by 28, said locking part being formed at its upper end with a knob 29 and at its lower end with a threaded bore (not shown) into which the stub axle 16 may be screwed.

The stub axle 16, the channel 18, and the locking part 28 together form a device fastening means, generally designated by reference 30.

The hose socket 26 is sealingly connected to a collection receptacle, generally designated by 31, preferably by means of a hose 32. The collection receptacle 31, shown in a cross-sectional view in FIG. 5, has a bottom portion 33 and a top portion 34 which are sealingly interconnected. The bottom portion 33 is manufactured from a stiffer material than the top portion 4. The top portion 34 is formed with an essentially centered handle 40 on its exterior and may be formed with folding initiation means 35 on its surface, essentially centered about the handle 40. The collection receptacle 31 is expandable into the configuration illustrated by the right-hand receptacle in FIG. 5, and compressible into the configuration shown by the left-hand collection receptacles in FIG. 5. The expansion and compression, may if required, be facilitated by the folding initiation means 35. However, such means are not a precondition for the function of the collection receptacle 31.

The operation of the device will appear from the description to follow. The flanged part 11 is associated with a container, generally designated by 36, via an aperture 37 therein. The flanged part 11 is secured in the aperture 37 in such a manner that it seals the edges of the aperture 37. In this position the holes 13 set the interior of the container 36 in communication with the environment. Initially, the container is empty (not shown) and it is of the type used in processes requiring containers that may be sealed off against the environment.

Five unused transfer members 1 are inserted into the magazine part 17 from underneath. The stop shoulders 27 are then turned laterally into locking engagement with a lateral recess 21 (see FIG. 2). When a transfer member 1 assumes its inserted position its collar 15 abuts against the lower portion of the magazine part 17. The upper portion of the holder 4 projects through the upper portion of the magazine part 17. In this starting position each hypodermic needle 5 is sealingly introduced into the membrane portion 9 to assume the position illustrated in FIG. 3. The magazine part 17 is then slid over the stub axle 16. The annular means 24, the pin 23 and the slit 25 co-operate to center the magazine part 17 in such a manner that the hypodermic needle 5 of each transfer member 1 will be positioned straight above a corresponding hole 13. The collar 15 of each transfer member 1 fits the corresponding seat 14. The locking part 28 is then screwed onto the stub axle 16, whereby the magazine part 17 is locked in the position illustrated in FIG. 2. In this locked position the material of the self-sealing collar 15 is compressed, exerting a sealing pressing action against the seat 14, whereby the holes 13 will be sealed against the environment.

Figure 3:
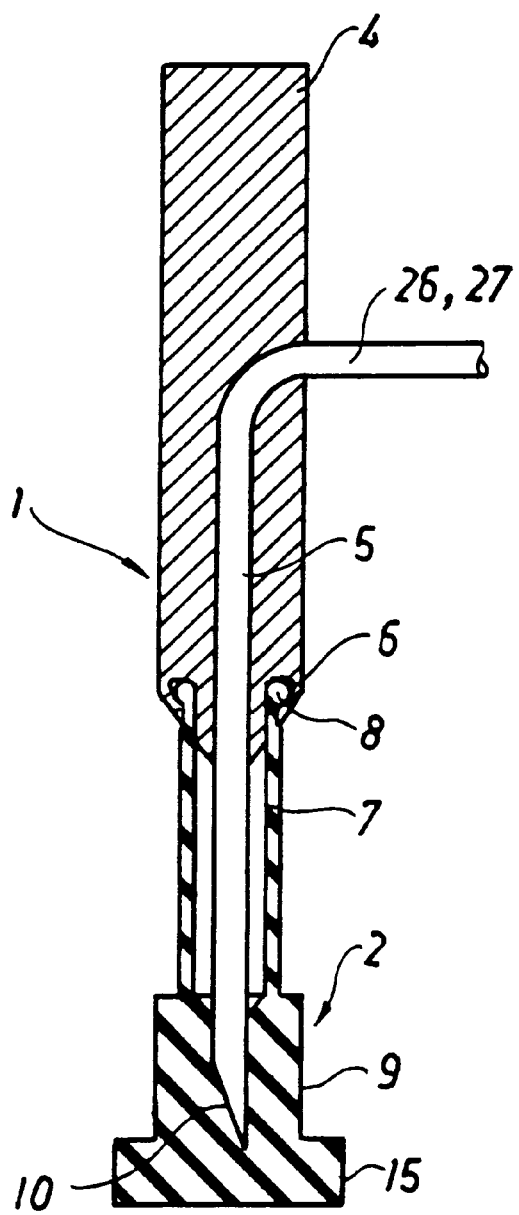
FIG. 3 is a schematical cross-sectional view showing a transfer member with the tip of a hypodermic needle disposed in a protective membrane portion.
Figure 4:
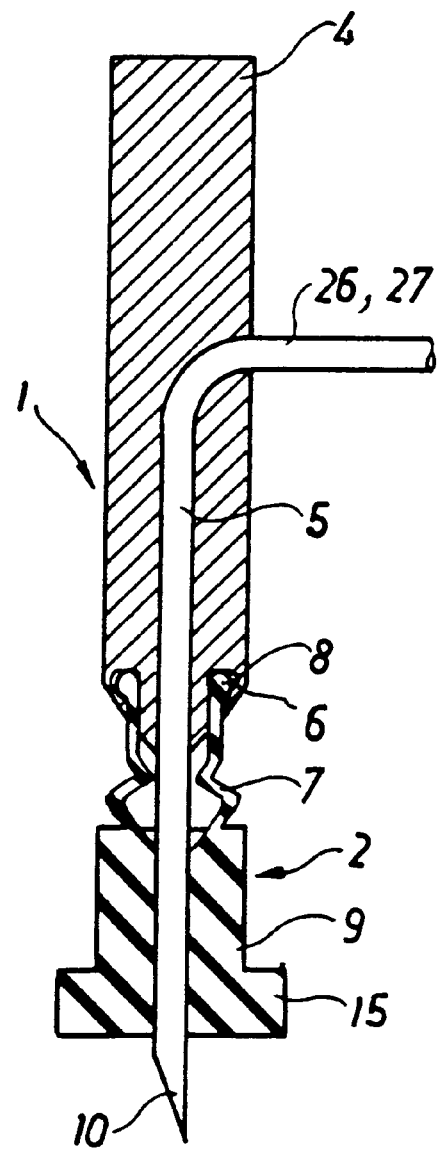
FIG. 4 is a schematical cross-sectional view of the transfer member of FIG. 3, according to which the tip of the hypodermic needle as penetrated the membrane portion.

The hypodermic needle 5, the hose 32 and the collection receptacle 31 form a unit that is sealed against the environment as long as the hypodermic needle 5 remains in the position illustrated in FIG. 3. The unit preferably is pre-sterilised. At their upper ends the collection receptacles 31 are formed with an aperture by means of which the receptacles may be suspended from hook means 38 on the container 36.

After the device thus having been secured to the container 36 in the manner described, the interior of the container 36 may be cleansed and sterilised in any known manner. During this procedure the inner face of the flanged part 11, the holes 13 and the lower part of the membrane portion 9 in contact with the interior of the tank are cleaned. All components of the device that come into contact with the interior of the container 36 thus will achieve the same degree of purity as the interior of the container 36, whereby the risks of contamination from these components are eliminated.

The container 36 is thereafter filled with a medium 39 to a level above the aperture 37 and the process inside the container may be initiated. When samples are to be withdrawn from the container 36 the stop shoulder 27 of one of the transfer members 1 is turned to dislodge it from its locking engagement with a lateral recess 21. The stop shoulder 27 is then displaced, and consequently also the hypodermic needle 5 and the bellows-shaped part 7, in the lengthwise direction of the groove 20 and the aperture 19, to the position illustrated in FIGS. 4 and 5 by reference 41, wherein the tip 10 of the hypodermic needle 5 has penetrated the membrane portion 9. In this position, the collection receptacle 31 is in sealed communication with the interior of the container 36. Since the tip 10 of the hypodermic needle 5 is pre-sterilised no contamination has arisen from this movement.

Figure 5:
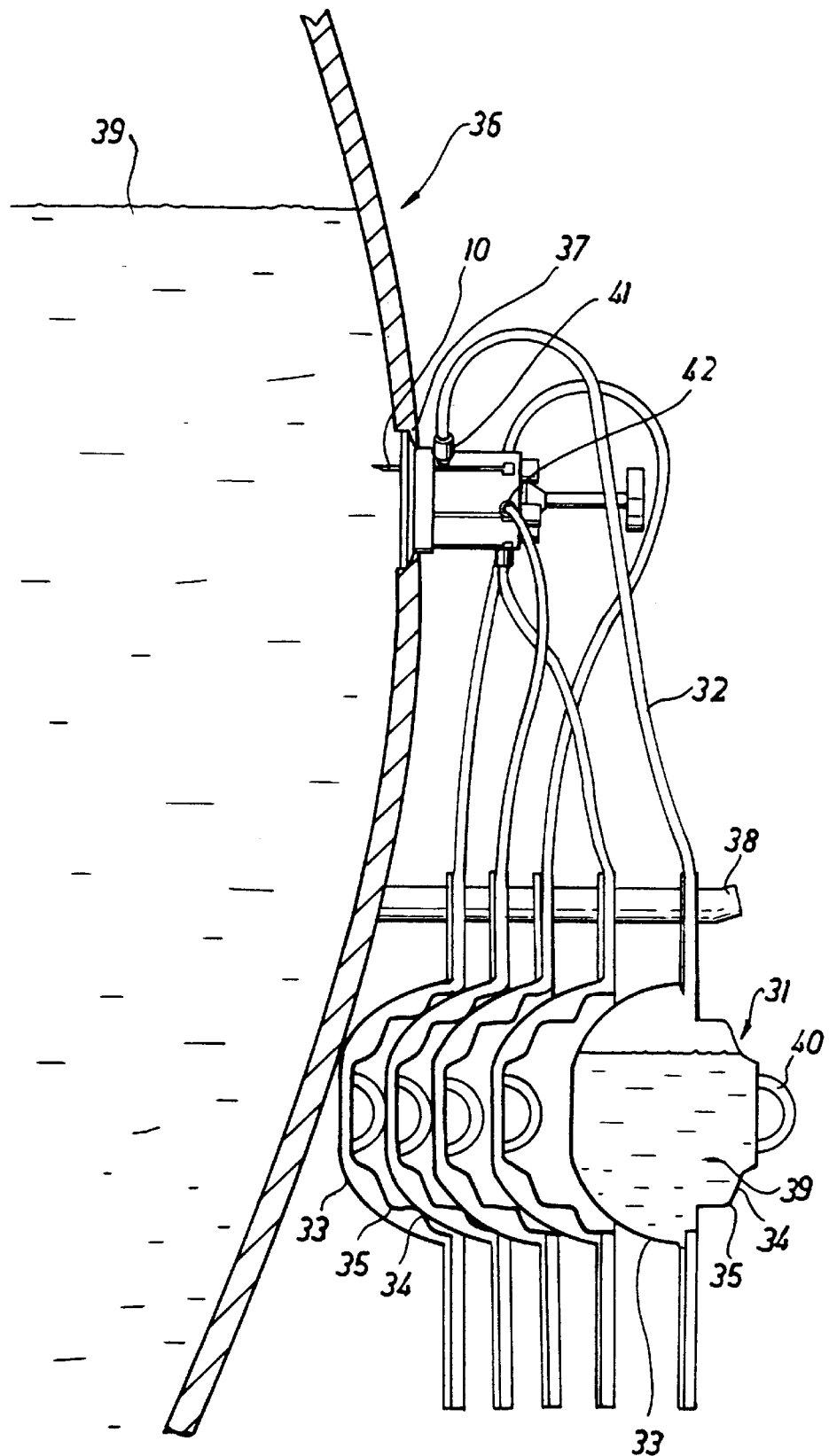
FIG. 5 is a schematic cross-sectional view illustrating the device when attached to a container.

Owing to the hydrostatic pressure caused by the level differences between the medium inside the container 36 and the collection receptacle 31, the medium 39 may in position 41 illustrated in FIG. 5 flow through the hypodermic needle 5, through the hose 32 to be collected in the collection receptacle 31. As the container 31 is being filled, it expands, and this expansion is facilitated by the above-mention folding initiation means 35. In order to speed up the filling operation the collection receptacle 31 may initially be expanded manually with the aid of the handle 40, causing a vacuum pressure to generate in the collection receptacle 31.

When a sufficient amount of the medium 39 has been withdrawn from the container 36, the transfer member 1 is retracted to the position illustrated in FIGS. 3 and 5 by reference 42 and it is locked in that position through the engagement of the stop shoulder 27 in the a lateral recess 21. This seals the channel formed by the needle 5 inside the membrane portion 9, whereby the tip 10 of the hypodermic needle 5 will be sealed inside the membrane portion 9. Since the hypodermic needle 5, the hose 32 and the collection receptacle 31 again form a closed, sealed system contamination of the withdrawn sample or contamination of the environment outside the container 36 are prevented. Owing to the lower collar 15 of the membrane portion 9 being pressed against the seat 14 of the fastening means 30 the sealing effect between these parts is improved, in addition to which the self-sealing capacity of the membrane portion 9 is increased.

The hose 32 leading to a filled collection receptacle 31 may thereafter be sealingly cut off by a cutter means (not shown), whereupon the collection receptacle 31 may be transported to a laboratory or the like while still all contamination risks are avoided. The cutting means could for example be a device of the kind that fuses together the two hose ends, or it could be a device which sealingly squeezes together the hose ends by means of clamps.

Five samples may be withdrawn by the device in accordance with the shown embodiment. The number of devices for a container 36 as well as the number of transfer members 1 for each device could, however, differ.

When the process in the container 36 has come to an end, the container is emptied, cleansed and disinfected from within. During this operation the components of the device that are exposed to the tank interior are cleansed. The locking part 28 may then be released and the magazine part 17 be pulled off from the stub axle 16 without risks of contaminating the environment. The entire magazine part 17 may then be exchanged for a new magazine part 17 that is loaded with unused transfer members 1. Alternatively, it is possible to replace used transfer members 1 in one and the same magazine part 17. As long as used hypodermic needles 5 are not pulled out of the membrane portion 9 the hypodermic needle 5 and the corresponding cut-off hose end form a closed, sealed system. Used hypodermic needles, hose parts and collection receptacles are destructed in a manner suitable considering the medium, for instance by incineration. The parts of the device which after use are to be destructed preferably are incinerated, since these parts as such are manufactured from a combustible material that does not emit noxious fumes. The magazine part 17 is then locked in the position as indicated above and the interior of the container 36 is cleaned and disinfected preparatory to a new process step.

The hose 32 of a filled collection receptacle 31 obviously need not be cut off for transportation of the sample when the magazine). part 17 is removed from the container 36. Instead, the transfer member 1 may be removed from the magazine part 17, and the transfer member 1, the hose 32, and the collection receptacle 31 be transported to a laboratory or the like. Alternatively, the hose 32 may be directly connected to analysis equipment, to another container or the like.

It is not either necessary to remove the magazine part 17 and the transfer member 1 each time the container 36 is emptied and cleaned, since the parts of the device that are exposed to the interior of the container 36 are imparted the same degree of purity as the container interior upon cleaning and disinfection thereof. Consequently, the device may be used in several processing steps without being removed, as long as the number of unused transfer members 1 is sufficiently large.

A second hose may be sealingly connected to the collection receptacle 31 or to the hose 32. At the end of the second hose a pre-sterilised syringe may be sealingly attached for transfer of the specimen to another container or the like. Furthermore, the second hose may be connected to a second transfer member 1. In this manner, the medium 39 may be withdrawn from a container 36 in a sealed condition and be introduced into a second container (not shown) in sealed condition by means of a device as described above. In this case a hypodermic needle 10 is introduced into the second container, whereupon the collection receptacle 31 is positioned above the level of the medium in the second container, whereupon the medium in sealed condition may be introduced into the container by means of the hydrostatic pressure. In order to facilitate the introduction of the medium the deformable upper portion 34 of the collection receptacle 31 may be compressed against the bottom portion 33.

Figure 6:
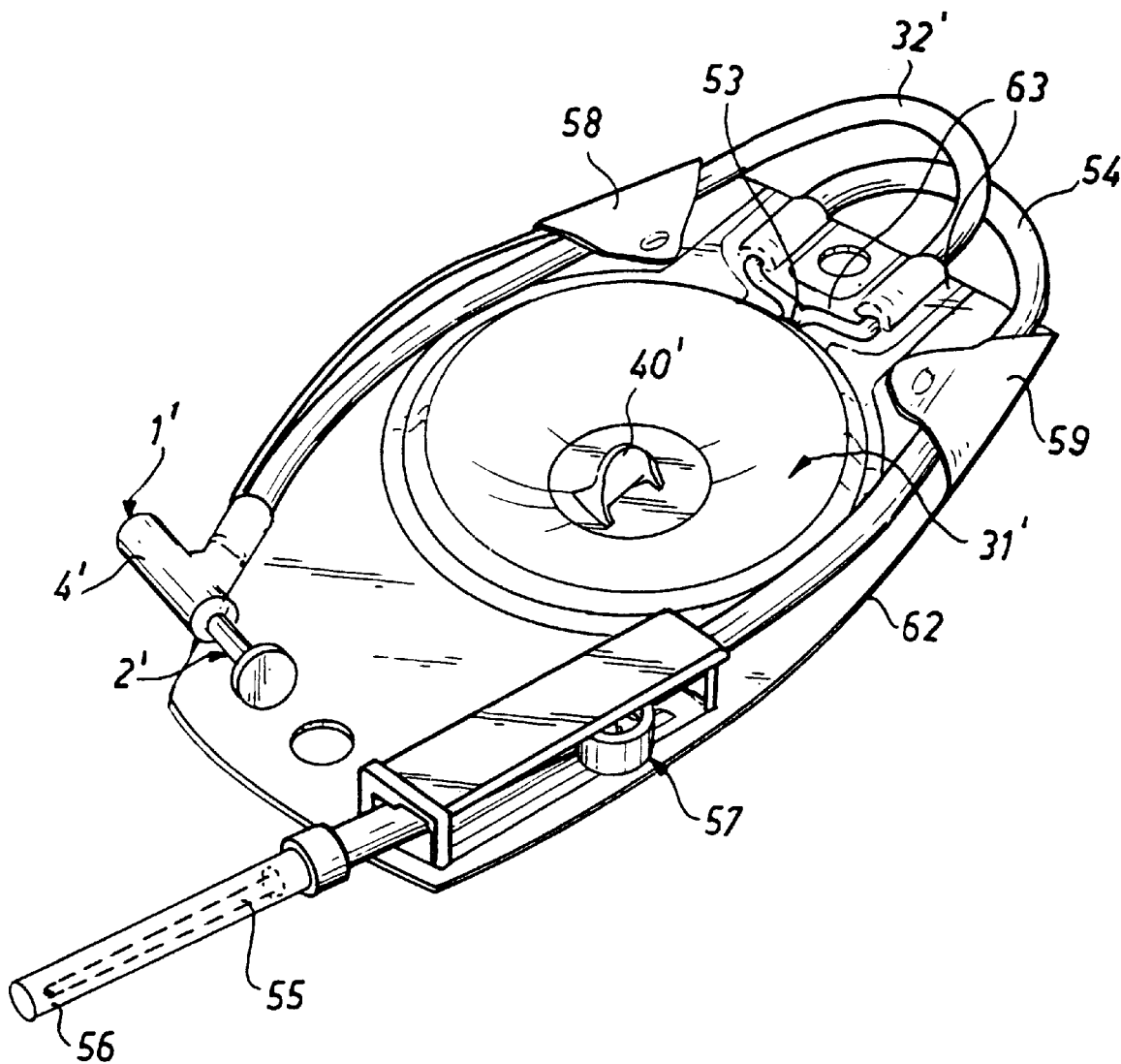
FIG. 6 is a schematic perspective view, showing an alternative embodiment of a collection receptacle in a compressed condition.
Figure 7:
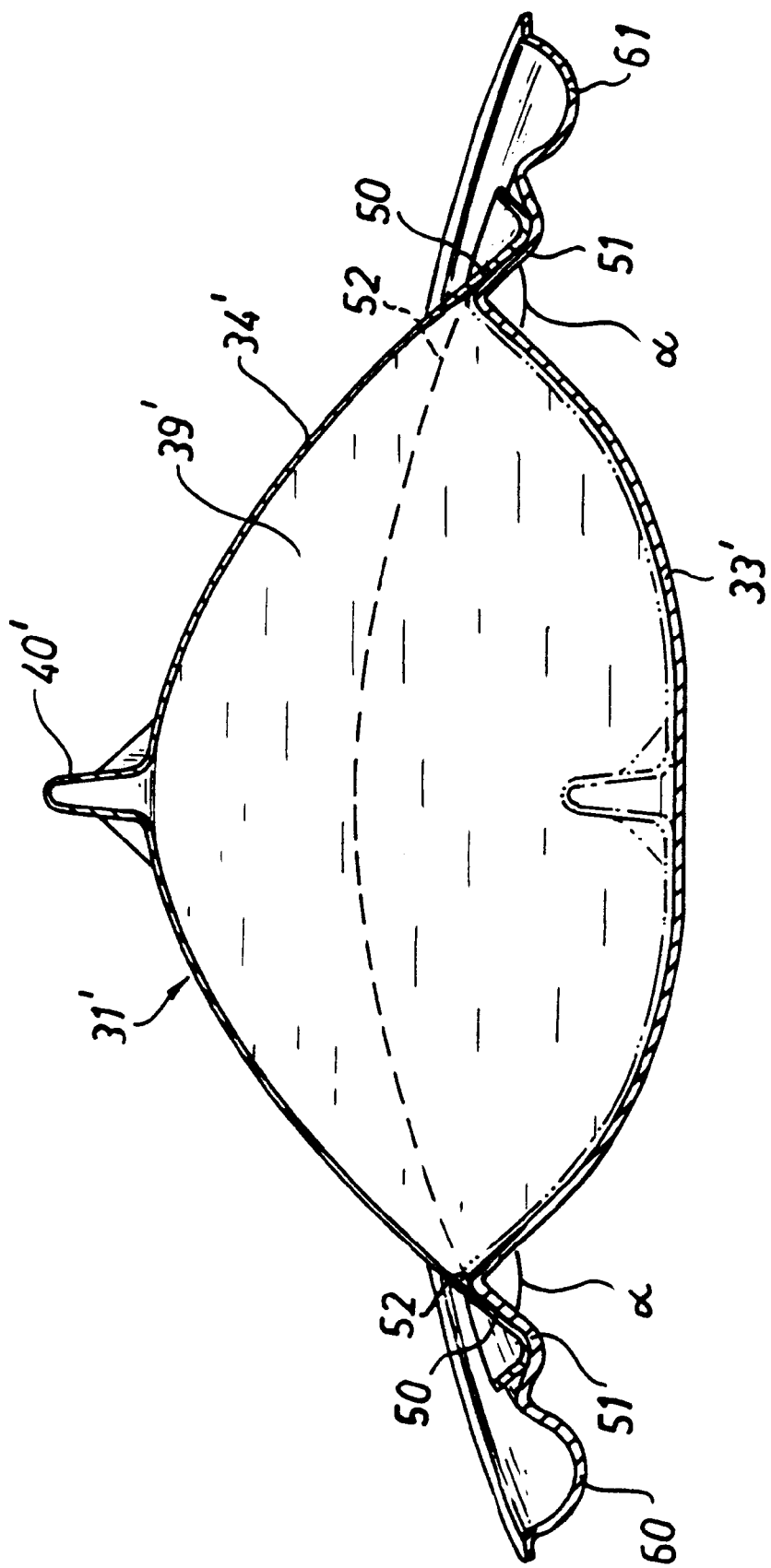
FIG. 7 is a shematical cross-sectional view of the collection receptacle illustrated in FIG. 6, showing said receptacle in an expanded position and also showing schematically, by means of a dash-and-dot line, the collection receptacle in its compressed condition.

FIGS. 6–7 illustrate a second embodiment of a collection receptacle 31'. Parts similar to those described with reference to FIGS. 1–5 have received the same references in FIGS. 6–7 but with the addition of a prime sign. The collection receptacle 31' comprises a first essentially arch-shaped part 33' and a second essentially arch-shaped flexible part 34'. In accordance with the embodiment illustrated the parts 33' and 34' are essentially domed and preferably are manufactured from a plastics material, the first part 33' preferably being manufactured from a material possessing a higher degree of rigidity than material of the second flexible part 34'. In FIG. 7 continuous lines illustrate the collection receptacle 34' in an expanded position in which it is filled with medium 39' whereas dash-and-dot-lines illustrate the receptacle in its compressed position. In the compressed position the second flexible part 34' is disposed adjacent the first part 33' to allow a collection receptacle 31' to be completely emptied of medium 39' that has collected therein. As appears from FIGS. 6–7 a handle 40' is provided on the second flexible part 34' to facilitate handling of the second flexible part 34' between the expanded position and the compressed position. However, it is easily understood that it is likewise possible to realise the shift from one position to the other in some other way, for example by making use of the hydrostatic pressure like in the first embodiment above.

The first part 33' and the second flexible part 34' are interconnected in an interconnection area 50 along a facing marginal portions of the parts. The joint or interconnection between the parts 33'–34' may be made for instance by gluing or welding. As appears from FIG. 7 the interconnection area 50 in accordance with the shown preferred embodiment extends essentially in parallel with the extension of the marginal areas of the second flexible part 34' in the expanded position. Owing to this arrangement the risk of bursting of the second flexible part 34' in the interconnection area 30' is reduced as is also the risk of tearing in the connection area 50 as the collection receptacle 51 is exposed to an excess pressure, e.g. in comparison with a structure wherein an interconnection area between the first and the second parts extends horizontally with respect to FIG. 7 (not shown).

Externally of its dome the first part 33' preferably is formed with an annular collar or flange 51 which extends along said interconnection area 50 and which is connected to the second flexible part 34' by being joined thereto in the interconnection area 50. The collar 51 and the first part 33' are interconnected in accordance with the shown embodiment along a peaked rim 52 bent at a preferably acute angle α, across which rim the second flexible part 34' may be shifted between the compressed position and the expanded position. Preferably, the interconnection area 50 extends exteriorly of said peaked rim 52. The rim 52 consequently acts as a "hinge" across which the second flexible part 34' moves between the expanded and the compressed positions. When the interconnection area 50 extends beyond said peaked rim 52, as is the case in accordance with the preferred embodiment, the "hinge" movement affects the interconnection area 50 less as this second flexible part 34' moves, as compared with what would be the case, had said interconnection for instance extended up to or terminated interiorly of said marginal area 50. The movement of the second flexible part 34 thus is effected in accordance with the embodiment in an area which is disposed interiorly of the interconnection area 50, imparting higher strength to the interconnection between the first part 33' and the second flexible part 34'.

As illustrated in FIG. 6 the collection receptacle 31' is formed with at least one channel 53 which in accordance with the embodiment shown extends through said interconnection area 50 and which in accordance with the shown embodiment is connected to a hose 32', the latter in turn being connected to a hypodermic needle disposed in a transfer member 1' of similar construction to that described above and which has a holder 4' and a seal means 2'. In this manner, the collection receptacle 31' thus is connected to the hypodermic needle of the transfer member 1'. In accordance with the shown embodiment the channel 53 is likewise by means of a second hose 54 connected to a hypodermic needle 55 known per se, which is provided in a close-fitting removable cover 56. A clamping device 57 known per se is arranged about the second hose 54 in accordance with the shown embodiment. The entire unit illustrated in FIG. 6 is preferably pre-sterilised and preferably forms a sealed unit prior to use.

The collection receptacle 31' and accessories are shown in FIG. 6 in a transportation position wherein the hoses 32' and 54 are disposed underneath flaps 58 and 59, respectively fastened by snap fasteners. The clamping device 57 and/or the hoses 32' and 54, respectively, and/or the transfer member 1 preferably are disposed in depressed parts in a holder 62 located around the collection receptacle 31' in order to provide improved stackability of the collection receptacle 31'. In accordance with the shown preferred embodiment the holder 62 is a continuation of the first part 33'. Consequently, for instance the hoses 32' and 54 may be disposed in the position of transportation in grooves 60 and 61, respectively, as seen in FIG. 7. Also the clamping device 57 is illustrated in FIG. 6 in a depressed position in the holder 62.

As appears from FIG. 6 the second flexible part 34' is formed in accordance with the shown embodiment with a portion 63 which for instance by welding or gluing is interconnected with the holder adjacent the channel 53 and the area of interconnection of the channel 53 with the respective hose 32', 54 to allow sealing interconnection of the respective hose 32', 54 with the collection receptacle 31'.

It is easily understood that via the collection receptacle 31' and a hypodermic needle arrangement 55, 56, 57 and/or directly, the transfer member 1' may be connected to another container, another collection vessel, analysis equipment, or some other form of receptacle, etcetera.

By the inventive construction a device is provided according to which the introduced and/or withdrawn medium is protected from contamination from the environment of the container 36. In addition a device is provided protecting the environment from the withdrawn and/or introduced medium. Owing to this device a representative specimen may be withdrawn from the container without involving or causing contamination risks. Because the device, when correctly used, eliminates contamination risks in the container and in its environment, the container may be disposed in an ordinary room with no particular strict requirements on cleanliness. Because a collars 15 of the different transfer members 1 are separate from one another upon sampling or introduction of medium into the container 36 there is no risk of cross-contamination between a first collar 15 and a second collar 15. Because it is clearly apparent from a filled collection receptacle 31; 31' or from a cut-off hose 32; 32'; 54 that the corresponding transfer member 1; 1' has been used the risk that a hypodermic needle 5 would be used twice by mistake is very small, which, had it occurred, could have involved a contamination risk. Because the hypodermic needle 5, the hose 32; 32', and the collection receptacle 31; 31' form a pre-sterilised sealed unit and because the parts of the device that are exposed to the container interior are cleansed and disinfected simultaneously with the cleaning and the disinfection of the container, the device has a contamination level corresponding to that of the container interior. Because the point on the hose 32; 32' where the cut is effected is sealed the joint can never contaminate the environment.

It is easily understood that certain deviations from the descried embodiment may be made. For instance the number of parts and the configuration of the fastening device 3 may be varied. In addition, the hose 32; 32' could for instance be a tube. The grooves 20 may run along the entire outer face of the magazine part 17 and a stop/locking device be arranged in the locking part 28, the function of which corresponds to that of the stop means and the locking means in the upper part of the groove 20 and the lateral recesses 21. The container 36 obviously could be in the form of a tank, a tube pipe or other type of vessel. All such of varieties and modifications that are encompassed by the basic inventive concept should be regarded to be within the scope of the appended claims.

We claim:

1. A device for one of introduction and withdrawal of a medium into a container having an aperture formed therein for receiving said device, said device comprising:

at least one removable, replaceable transfer member for transferring a medium into and out of the container, said transfer member comprising a holder, a seal for sealing said aperture, a hypodermic needle having a tip, said needle supported within said holder in a longitudinal direction thereof, wherein the seal has a first end comprised of a bellows-shaped part sealingly attached to said holder, and a second end comprising a self-sealing membrane portion interiorly formed at an end of said bellows part, said membrane portion for sealing said aperture of said container, wherein said bellows-shaped part surrounds said needle and is deformable in a longitudinal direction, said membrane portion pierceable by the tip of the needle to form a sealable channel;

a fastening device for sealingly securing the transfer member via the seal with the aperture of the container, thereby forming a closed system, said fastening device comprising a flanged part sealingly secured in the aperture and formed with at least one hole therethrough in communication with an interior of said container, a magazine part for removable securement of said at least one transfer member, and a fastening and centering means for removable locking of the magazine part to a flanged part in a position wherein the membrane portion sealingly abuts against the hole of the flanged part so as to accept the hypodermic needle for introduction into and withdrawal from the container through the membrane portion and the hole.

2. The device as claimed in claim 1, wherein the fastening device comprises a stub axle attached to an upper face of the flanged part and which projects perpendicularly therefrom, said magazine part including a channel therein through which the stub axle extends when in a locked position with the magazine part, said locking part attached to the stub axle so as to interconnect the magazine part and the flanged part.

3. The device as claimed in claim 2, wherein the membrane portion is formed with a bottom collar that is clamped between the flanged part and the magazine part when in a locked position.

4. The device as claimed in claim 3, wherein the transfer member includes a stop shoulder formed thereon and the magazine part has a top end, a bottom end, a peripheral surface, and a centrally located, longitudinally extending throughbore for receiving said stub axle therein, at least one longitudinally extending aperture disposed between said central throughbore and said peripheral surface, a groove formed in the peripheral surface so as to communicate with said aperture, said groove having an upper end formed with at least one lateral recess, said transfer member and the stop shoulder being movable in the aperture and in the groove in the longitudinal direction of the hypodermic needle between a first and locked position, in which the needle is in communication with the interior of the container and a second position, in which the stop shoulder is disposed in the upper end of the groove and in which the tip of the hypodermic needle is sealingly disposed inside the membrane portion, said stop shoulder arranged, in said second position, to be displaced in response to a turning movement, into engagement with a lateral recess to lock the transfer member in said position.

5. The device as claimed in claim 1, wherein the hypodermic needle is sealingly connected to a collection receptacle, said collection receptacle being expandable upon withdrawal of medium from the container and compressible upon introduction of medium into the container.

6. The device as claimed in claim 5, wherein the collection receptacle is connected to the hypodermic needle via a hose, and in that a cutting device is provided to sealingly cut said hose in order to free the collection receptacle from the hypodermic needle.

7. The device as claimed in claim 5 wherein the collection receptacle has a first part and a second flexible part, and a handle arranged in said flexible part, said handle allowing a vacuum to be produced in the collection receptacle upon pulling on the handle as said receptacle is being expanded during withdrawal of said medium.

8. The device as claimed in claim 5, wherein the collection receptacle has a first domed part having a marginal area and a second flexible domed part having a second marginal area, said parts being interconnected along respective facing marginal areas in an interconnection area, the second flexible part movable between a first compressed position wherein said second position bulges into the first part and a second expanded position in which said second part bulges outwards from the first part.

9. The device as claimed in claim 8, wherein the collection receptacle is formed with a channel which extends through said interconnection area.

10. The device as claimed in claim 9, wherein said channel is connectable by means of a second hose to one of the group consisting of a second container, another collection receptacle, analysis equipment and the hose.

11. The device as claimed in claim 8, wherein the first part and the second flexible part are arranged in said first compressed position, closely adjacent one another to allow the collection receptacle to be emptied of all medium.

12. The device as claimed in claim 8, wherein in the expanded position, the interconnection area extends essentially in parallel with the extension of the marginal area of the second flexible part.

13. The device as claimed in claim 8, wherein said first part is delimited by a collar extending along said interconnection area and being connected to said second, flexible part.

14. The device as claimed in claim 13, wherein said collar and said first part are interconnected along a peaked rim formed at an acute angle ($\alpha$), across which rim the second, flexible portion is moveable between the first compressed position and the second expanded position, and wherein the interconnection area extends exteriorly of said rim.

* * * * *